United States Patent
Locke

(10) Patent No.: US 8,043,861 B2
(45) Date of Patent: Oct. 25, 2011

(54) METHODS AND APPARATUS FOR DETECTING EXPOSURE TO HAZARDOUS SUBSTANCES

(75) Inventor: Edward P. Locke, Norfolk, VA (US)

(73) Assignee: K & M Environmental, Inc., Virginia Beach, VA (US)

( * ) Notice: Subject to any disclaimer, the term of this patent is extended or adjusted under 35 U.S.C. 154(b) by 1614 days.

(21) Appl. No.: 11/226,538

(22) Filed: Sep. 14, 2005

(65) Prior Publication Data

US 2007/0238192 A1   Oct. 11, 2007

Related U.S. Application Data

(60) Provisional application No. 60/611,977, filed on Sep. 22, 2004.

(51) Int. Cl.
G01N 21/75   (2006.01)

(52) U.S. Cl. ........ 436/167; 436/164; 422/401; 422/430; 422/416; 422/83; 422/88; 250/472.1

(58) Field of Classification Search .................. 422/119, 422/401, 409, 416, 430, 83, 88; 436/2, 58, 436/55, 164, 167; 250/472.1
See application file for complete search history.

(56) References Cited

U.S. PATENT DOCUMENTS

| | | |
|---|---|---|
| 3,950,980 A | 4/1976 | Braun et al. |
| 4,205,043 A | 5/1980 | Esch et al. |
| H264 H | 5/1987 | Nicholson et al. |
| 4,772,560 A | 9/1988 | Attar |
| 4,900,936 A | 2/1990 | Evers |
| 4,946,705 A | 8/1990 | Manning et al. |
| 5,328,847 A | 7/1994 | Case et al. |
| 5,692,029 A | 11/1997 | Husseiny et al. |
| 5,866,430 A | 2/1999 | Grow |
| 5,891,649 A | 4/1999 | Kidwell et al. |
| 5,947,369 A | 9/1999 | Frommer et al. |
| 6,022,748 A | 2/2000 | Charych et al. |
| 6,140,651 A | 10/2000 | Justus et al. |
| 6,284,198 B1 * | 9/2001 | Kirollos et al. .................. 422/87 |
| 6,306,598 B1 | 10/2001 | Charych et al. |
| 6,468,759 B1 | 10/2002 | Charych |
| 6,485,987 B1 | 11/2002 | Charych et al. |
| 6,564,620 B1 | 5/2003 | Jaeger |

(Continued)

FOREIGN PATENT DOCUMENTS

DE    3735176 A1    4/1989

OTHER PUBLICATIONS

European Search Report, Feb. 3, 2009, 9 pages.

(Continued)

*Primary Examiner* — Lyle Alexander
(74) *Attorney, Agent, or Firm* — Armstrong Teasdale LLP

(57) ABSTRACT

An apparatus for detecting exposure to at least one hazardous substance is provided. The apparatus includes a body having a plurality of openings, and an attachment mechanism coupled to the body. Each opening is sized to receive a cassette for detecting the presence or absence of at least one hazardous substance. The cassette can include a colorimetric sensor having a base layer fabricated from a hydrophobic film, a colorimetric coating for covering the hydrophobic film, and at least one hydrophobic membrane for controlling the exposure of the specific substance to the colorimetric coating.

15 Claims, 4 Drawing Sheets

U.S. PATENT DOCUMENTS

| | | |
|---|---|---|
| 6,569,630 B1 | 5/2003 | Vivekananda et al. |
| 6,582,657 B2 | 6/2003 | Warner et al. |
| 6,617,963 B1 | 9/2003 | Watters et al. |
| 6,627,891 B1 | 9/2003 | Warner et al. |
| 6,783,989 B1 | 8/2004 | Zakin |
| 2002/0068016 A1 | 6/2002 | Warner et al. |
| 2003/0098354 A1 | 5/2003 | Steklenski et al. |
| 2003/0099582 A1 | 5/2003 | Steklenski et al. |
| 2003/0129759 A1 | 7/2003 | Lewis et al. |
| 2003/0150983 A1 | 8/2003 | Nishizawa et al. |
| 2003/0211618 A1 | 11/2003 | Patel |
| 2004/0069046 A1 | 4/2004 | Sunshine et al. |
| 2004/0099814 A1 | 5/2004 | Brand et al. |
| 2004/0116795 A1 | 6/2004 | Collins et al. |
| 2004/0141879 A1 | 7/2004 | Loomis et al. |
| 2004/0159803 A1 | 8/2004 | Akselrod et al. |

OTHER PUBLICATIONS

Geodert, Michel G.; Encyclopedia of Analytical Chemistry; Oct. 2000; 84 pages.

PCT International Search Report, for International Application No. PCT/US 05/33088, Filed on Sep. 15, 2005, 2 pages.

* cited by examiner

METHODS AND APPARATUS FOR DETECTING EXPOSURE TO HAZARDOUS SUBSTANCES

CROSS REFERENCE TO RELATED APPLICATIONS

This application claims priority to Provisional Patent Application No. 60/611,977, filed Sep. 22, 2004, which is hereby incorporated by reference in its entirety.

STATEMENT REGARDING FEDERALLY SPONSORED RESEARCH & DEVELOPMENT

The government of the United States of America has certain rights in this invention pursuant to SBIR Contract No. M67854-04-C-5018 awarded by the U.S. Marine Corps System Command.

BACKGROUND OF THE INVENTION

This invention relates generally to detecting exposure to hazardous substances and, more particularly, to methods and apparatus for detecting exposure to hazardous substances.

Throughout the world, at least some individuals may be at risk of exposure to hazardous substances. For example, such individuals may include factory workers, military personnel and first responders. Accordingly, it is not uncommon today to provide such individuals at risk with a device to detect the presence of hazardous substances. Such detection devices may include, but are not limited to, colorimetric badges, colorimetric tubes and electrochemical monitors. However, at least one drawback to these known detection devices is that such devices are typically limited to detecting only one type of chemical, a single family of chemicals, or are non-specific as to the chemicals they do detect. For example, if an individual wants to detect five different chemicals using colorimetric tube technology, five different colorimetric tubes would be required. Moreover, at least some of these known detection devices are unable to withstand a wide range of environmental conditions, including water immersion. For example, at least some known colorimetric badges may malfunction if immersed in water, because the sensor material can become mechanically compromised or a component of the sensor can dissolve when exposed to water.

A chemical detection device that could be worn by a user for detecting a plurality of hazardous or potentially hazardous substances could enable the user to take certain safety precautions to better protect the user's well being. Moreover, if a user is exposed to a hazardous substance and the user becomes ill, such a detection device may facilitate any medical treatment the user may receive, and consequently, may improve the user's chances of recovery. Furthermore, a chemical detection device capable of withstanding a plurality of environmental conditions would increase the number of potential users or the number of potential situations in which the device could be used.

BRIEF DESCRIPTION OF THE INVENTION

In one aspect, an apparatus for detecting exposure to at least one hazardous substance is provided. The hazardous substance detection apparatus includes a body and at least one removable cassette received in the body. Each removable cassette is configured to detect the presence of at least one predetermined hazardous substance.

In another aspect, a field configurable apparatus for detecting exposure to at least one hazardous substance is provided. The apparatus includes a body having at least one opening, and at least one cassette removably received in the body. Each cassette is positioned in one of the openings and includes at least one of a colorimetric sensor configured to detect the presence of at least one predetermined hazardous substance, and a collection medium configured to collect hazardous substances.

In another aspect, a cassette sized to be removably received in a hazardous substance detection apparatus is provided. The cassette includes at least one of a colorimetric sensor configured to change color upon detection of at least one predetermined hazardous substance, and a collection medium configured to collect hazardous substances.

In another aspect, a method for detecting a hazardous substance using a field configurable hazardous substance detection apparatus is provided. The method includes positioning a field configurable hazardous substance detection apparatus in an area of interest, configuring the detection apparatus to detect at least one predetermined hazardous substance, and monitoring the detection apparatus to determine if a hazardous substance has been detected by the detection apparatus. The detection apparatus includes a body having at least one opening, and at least one cassette removably received in the body. Each cassette is positioned in one of the openings and includes at least one of a colorimetric sensor configured to detect the presence of at least one predetermined hazardous substance, and a collection medium configured to collect hazardous substances.

DETAILED DESCRIPTION OF THE INVENTION

Example embodiments of methods and apparatus for facilitating a detection of a plurality of hazardous or potentially hazardous substances are described herein in detail. The apparatus, referred to herein as the chemical detection device, utilizes a reusable body, in which more than one cassette can be inserted. Each cassette detects the presence or absence of a particular hazard, such as a toxic industrial chemical, a chemical warfare agent, a biological threat, or radiation by changing color when exposed to the hazard. Each cassette can be inserted into, and removed from, the reusable body by the user, thus, enabling the device to be easily configured for the specific needs of a user. For example, if a user is concerned with exposure to phosgene, chlorine and hydrogen sulfide, then the user inserts a cassette adapted to detect each of these chemicals into the reusable body. If at a later time, that same individual is concerned only with carbon monoxide, then the user can reconfigure the device by inserting a carbon monoxide cassette into the body.

The systems and processes are not limited to the specific embodiments described herein. In addition, components of each system and each process can be practiced independently and separately from other components and processes described herein. Each component and process also can be used in combination with other assembly packages and processes.

Figure 1:
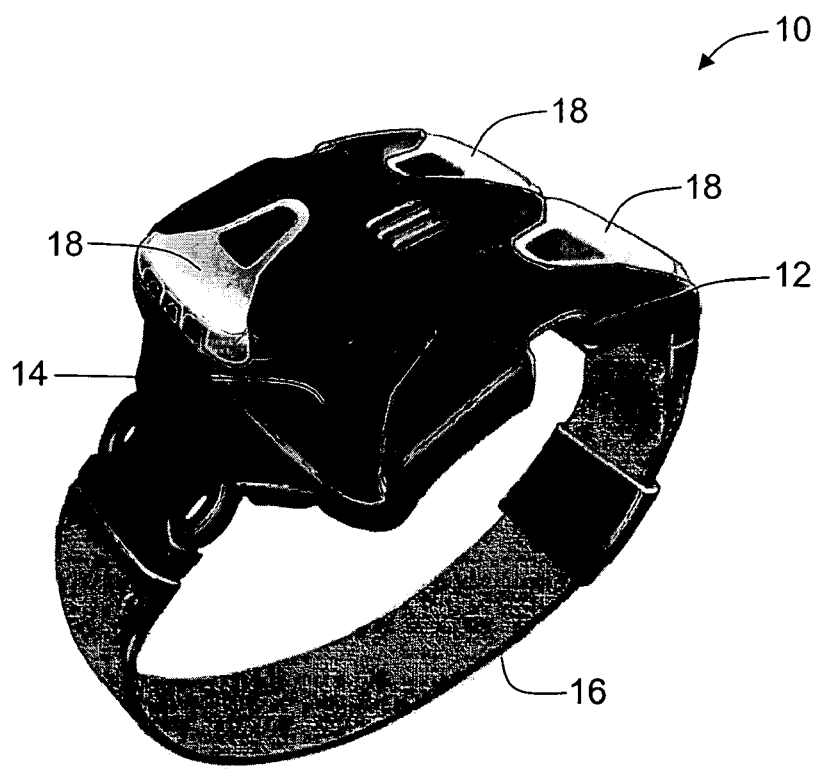
FIG. 1 is a perspective view of an example embodiment of a chemical detection device arranged in a four-cassette configuration.

FIG. 1 is a perspective view of an example embodiment of a chemical detection device 10 arranged in a four-cassette configuration. Chemical detection device 10 includes a body 12 having a plurality of openings 14, and a strap 16. In one embodiment, body 12 is reusable and strap 16 is adjustable. In alternate embodiments, any suitable attachment mechanism can be used in place of strap 16, for example, clips, fasteners, ties, and the like. Each opening 14 is sized to receive a cassette 18 therein. Each cassette 18 detects the presence or absence of a particular hazard, such as a toxic industrial chemical, a chemical warfare agent, a biological threat or radiation by changing color in the presence of the hazard. Cassette 18 can be inserted into, and/or removed, from body 12 by a user, thereby enabling the device to be easily configured for the specific needs of the individual.

Figure 2:
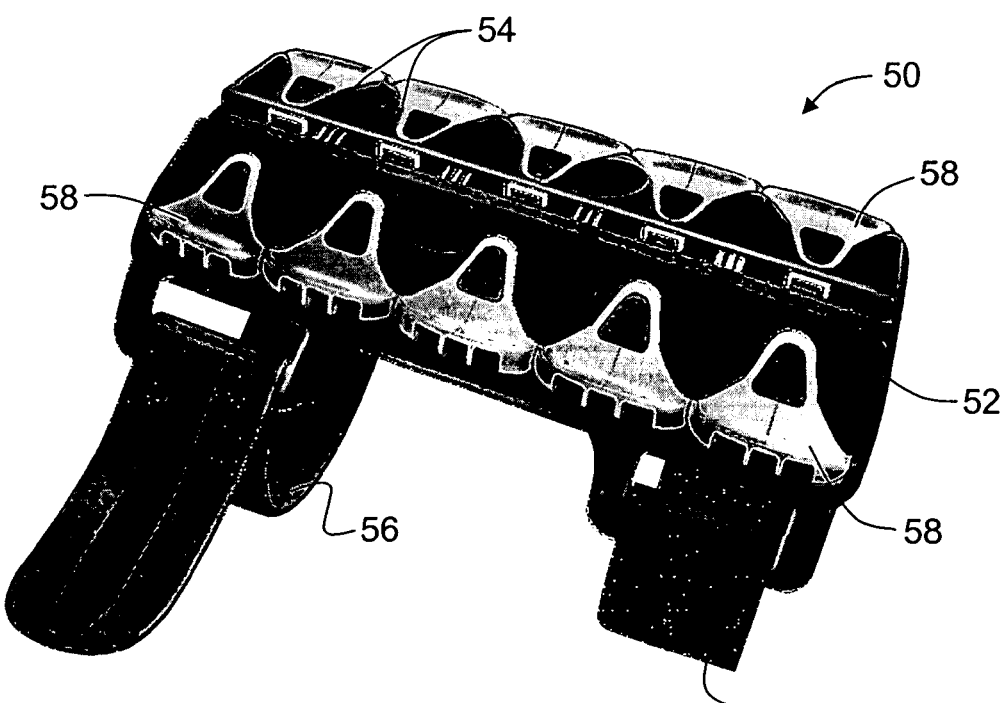
FIG. 2 is a perspective view of another embodiment of a chemical detection device arranged in a ten-cassette configuration.
Figure 6:
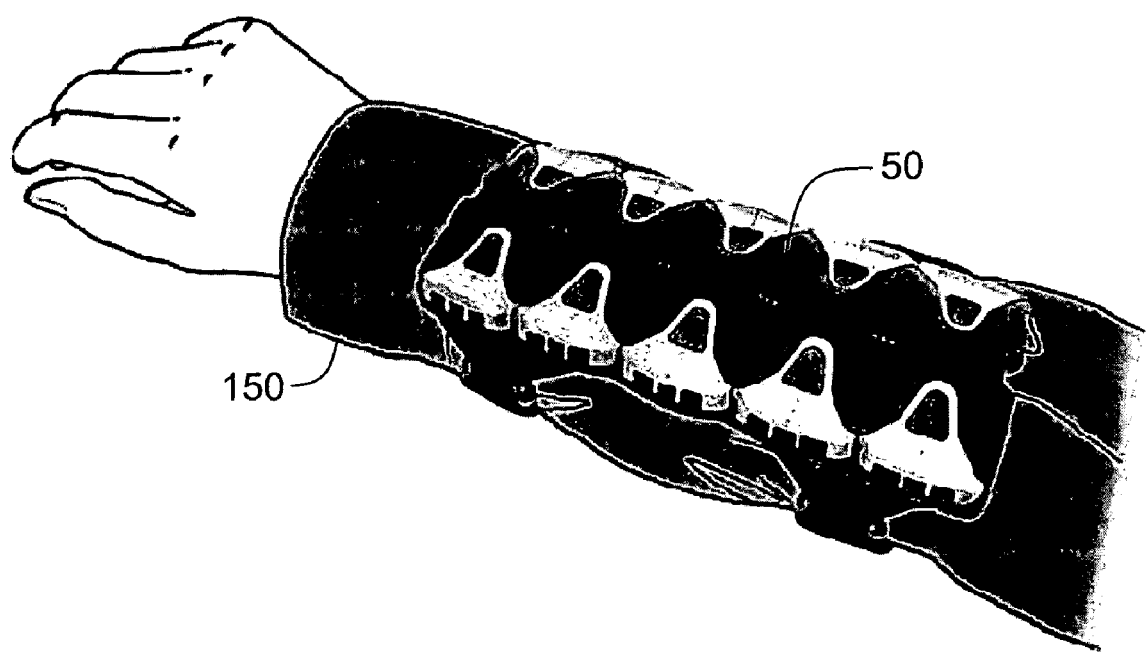
FIG. 6 is a perspective view of the chemical detection device shown in FIG. 2 coupled to a user's arm.

FIG. 2 is a perspective view of another embodiment of a chemical detection device 50. Chemical detection device 50 is arranged in a ten-cassette configuration. Chemical detection device 50 includes a body 52 having a plurality of openings 54, and at least one strap 56. In one embodiment, body 52 is reusable and strap 56 is adjustable. Each opening 54 is sized to receive a cassette 58 therein. Each cassette 58 detects the presence or absence of a particular hazard, such as a toxic industrial chemical, a chemical warfare agent, a biological threat or radiation by changing color when exposed to the hazard. Each cassette can be inserted into and removed from body 52 by a user, thereby enabling the device to be easily configured for the specific needs of the individual. FIG. 6 is a perspective view of chemical detection device 50 coupled to an arm 150 of a user.

Figure 3:
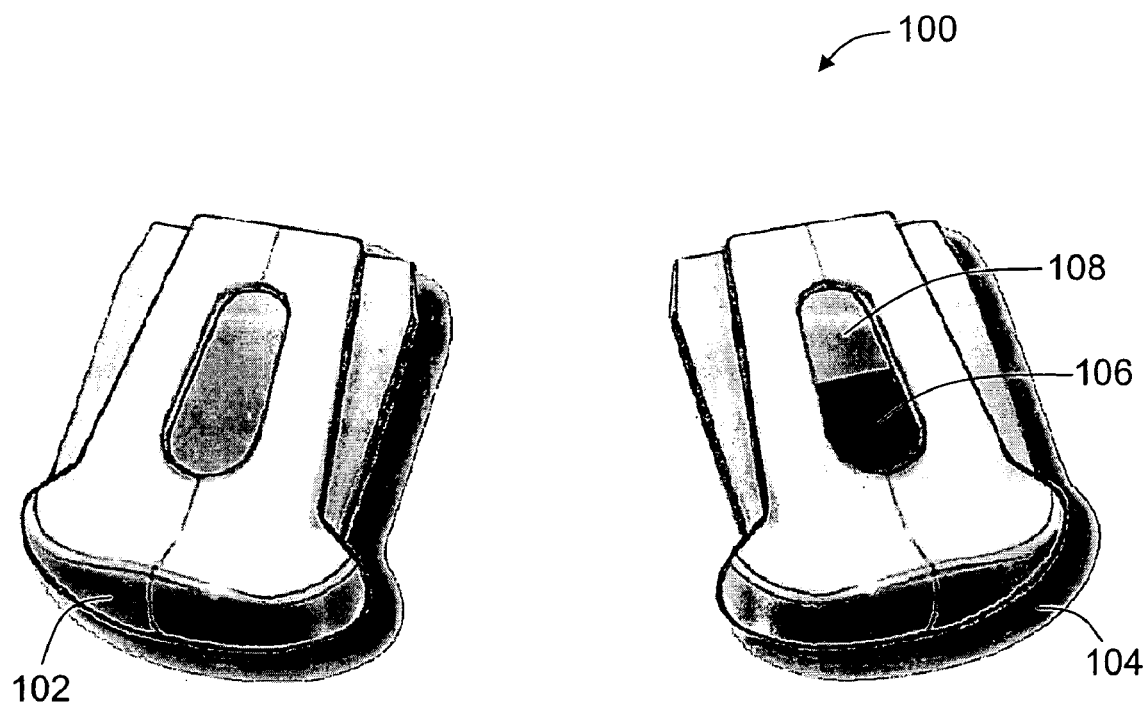
FIG. 3 is a perspective view of two cassettes used with the chemical detection devices shown in FIGS. 1 and 2 wherein the cassette illustrated on the left has not been subjected to a chemical exposure and the cassette illustrated on the right has been subjected to a chemical exposure.

FIG. 3 is a perspective view of two cassettes 100 used with chemical detection device 10 (shown in FIG. 1). Cassettes 100 include a first cassette 102 and a second cassette 104. In the example embodiment, cassette 102 illustrates how a cassette may appear before being subjected to a chemical exposure. In contrast, cassette 104 illustrates how a cassette may appear after being exposed to a chemical exposure. More specifically, in the example embodiment, cassette 104 indicates exposure to a chemical hazard by showing a color change 106 within a portion of window 108. It should be noted that the manner shown herein for indicating a chemical exposure (i.e., a color change) is for illustration purposes and, as such, other patterns or techniques not described herein could also be used to indicate that a cassette has been exposed to a chemical exposure.

Figure 4:
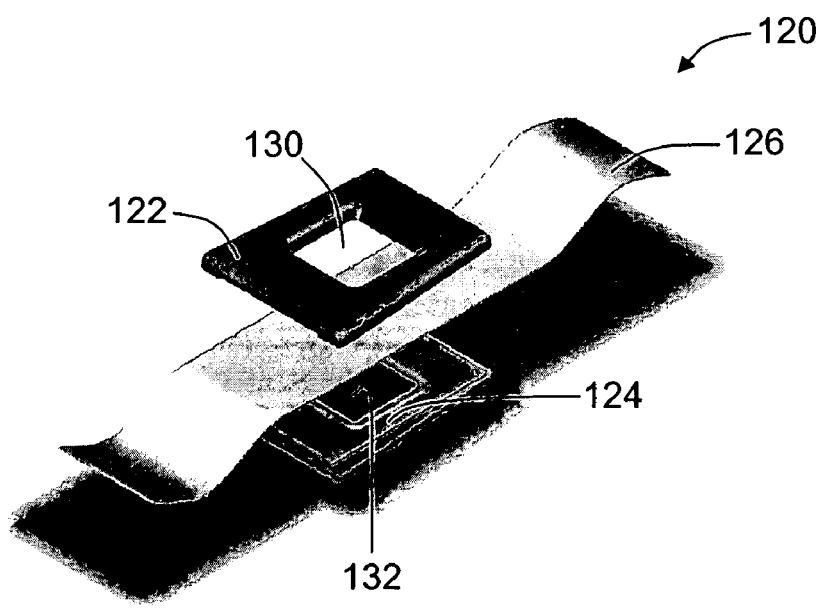
FIG. 4 illustrates one embodiment of a cassette from the chemical detection device shown in FIG. 1.
Figure 5:
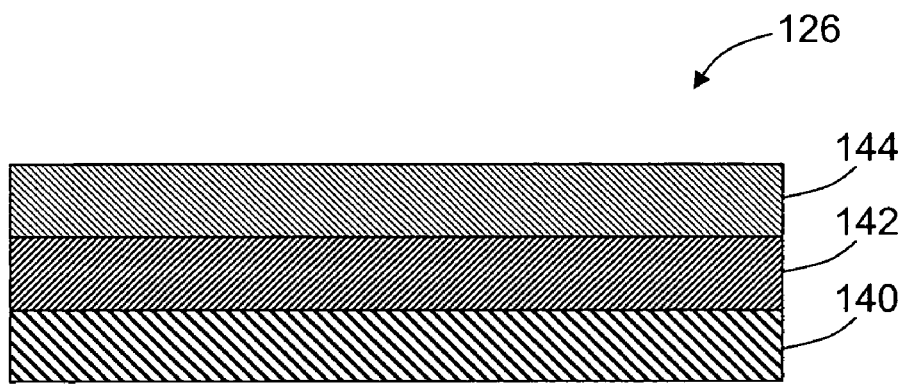
FIG. 5 is a sectional schematic illustration of the colorimetric sensor of the chemical detection device shown in FIG. 1.

FIG. 4 illustrates one embodiment of a cassette 120 from chemical detection device 10 (shown in FIG. 1). Cassette 120 includes a top frame 122, a bottom frame 124, and a colorimetric sensor 126 positioned between top frame 122 and bottom frame 124. In the example embodiment, and referring also to FIG. 5, colorimetric sensor 126 includes a base layer 140 fabricated from a hydrophobic film, a colorimetric coating 142 covering the hydrophobic film, and at least one hydrophobic membrane 144 which controls the amount of target gas which penetrates to colorimetric coating 142.

Top frame 122 includes an opening 130, and bottom frame 124 includes an opening 132. In the exemplary embodiment, top frame 122 and bottom frame 124 are sealed on the outside by ultrasonically welding the top and bottom frames 122 and 124 together near the outer edge of cassette 120. In another embodiment, a seal around openings 130 and 132 is created through a tongue in groove configuration, either with or without a gasket.

In another embodiment, cassette 120 includes one hydrophobic membrane 144, or a plurality of similar or different hydrophobic membranes 144, to precisely control the amount of target gas which penetrates to colorimetric coating 142. Also, in another embodiment, hydrophobic membrane 144 is configured so that macroscopic water is not permitted to contact colorimetric coating 142. In another alternate embodiment, hydrophobic membrane 144 is configured so that a predetermined controlled amount of water or water vapor is permitted to contact colorimetric coating 142. One exemplary method of applying a hydrophobic membrane to colorimetric coating 142 is through solvent welding.

In the exemplary embodiment, chemical detection device 10 (shown in FIG. 1) including cassettes 100 (shown in FIG. 3) is substantially waterproof. In one embodiment, device 10 is substantially waterproof against exposure to the environment such as rain, or immersion in water at slightly over 1 atmosphere. In another embodiment, device 10 is substantially waterproof against immersion in water at about 1 atmosphere or higher. Chemical detection device 10 is configured to be substantially waterproof using one or more of the following features: (1) colorimetric material 142 is coated on a thin hydrophobic film 140, (2) colorimetric coating 142 is formulated so that it has little or no impact from immersion in water, (3) colorimetric coating 142 is covered with a hydrophobic membrane 144 that permits a controlled amount of target gases to penetrate, but does not permit macroscopic water to penetrate, (4) hydrophobic membrane 144 is sealingly attached to colormetric coating 142 and/or hydrophobic film 140 to prevent water infiltration, and (5) cassette 100 includes a seal around any area of potential water infiltration.

Figure 7:
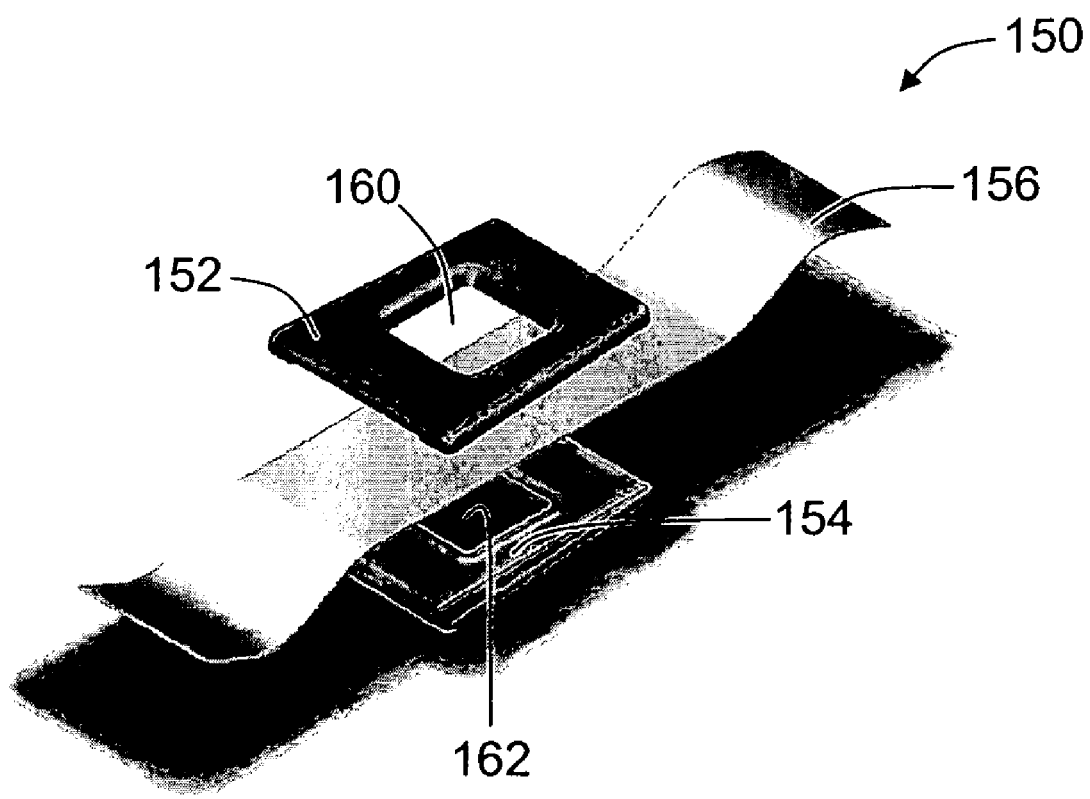
FIG. 7 illustrates another embodiment of a cassette from the chemical detection device shown in FIG. 1.

FIG. 7 illustrates another embodiment of a cassette 150 from chemical detection device 10 (shown in FIG. 1). Cassette 150 includes a top frame 152, a bottom frame 154, and a collection medium 156 positioned between top frame 152 and bottom frame 154. In this exemplary example embodiment, collection medium 156 is configured to collect hazardous substances. The collected hazardous substances can then be analyzed in a laboratory. Collection medium 156 can be any suitable solid sorbent, for example a cloth material impregnated with a polymer, zeolites, carbon, and polymer matrices that react with the hazardous material to collect the material. The solid sorbent material can function by adsorption or absorption.

Top frame 152 includes an opening 160, and bottom frame 154 includes an opening 162. In the exemplary embodiment, top frame 152 and bottom frame 154 are sealed on the outside by ultrasonically welding the top and bottom frames 152 and 524 together near the outer edge of cassette 150. In another embodiment, a seal around openings 150 and 152 is created through a tongue in groove configuration, either with or without a gasket.

The chemical detection device, which may be worn by a user (see FIG. 6), is configured to detect a plurality of hazardous or potentially hazardous substances. The chemical detection device can also be attached to an unmanned manipulator, for example, an unmanned vehicle, a robot arm, and the like, to position the detection device in an area of interest. Also, the chemical detection device can be attached directly to a surface of a structure, for example a wall, a door, or a ceiling. The chemical detection device enables the user to take certain safety precautions to better protect the user's well being. Moreover, if a user is exposed to a hazardous substance and the user becomes ill, the chemical detection device may facilitate any medical treatment the user may receive, and consequently, may improve the user's chances of recovery. Furthermore, the chemical detection device is waterproof and is configured to withstand a plurality of environmental conditions.

While the invention has been described in terms of various specific embodiments, those skilled in the art will recognize that the invention can be practiced with modification within the spirit and scope of the claims.

What is claimed is:

1. A hazardous substance detection apparatus comprising: a body comprising at least two openings; and
at least two removable cassettes received in said body, each said removable cassette positioned in one of said openings and comprises at least one of a colorimetric sensor configured to change color upon detection of a predetermined hazardous substance, and a collection medium configured to collect hazardous substances,
said colorimetric sensor comprising:
a colorimetric layer deposited onto a base layer; and
at least one hydrophobic membrane positioned adjacent said colorimetric layer, said at least one hydrophobic membrane configured to control an amount of gas permitted to penetrate said membrane and contact said colorimetric layer, said at least one hydrophobic membrane attached to at least one of said colorimetric layer and said base layer to seal and prevent water infiltration of said colorimetric layer.

2. An apparatus in accordance with claim 1 further comprising at least one attachment mechanism coupled to said body.

3. An apparatus in accordance with claim 1 wherein said base layer comprises a hydrophobic film;
said colorimetric layer comprises a colorimetric coating deposited on at least one surface of said base layer.

4. An apparatus in accordance with claim 1 wherein said hydrophobic membrane is configured so that macroscopic water is not permitted to contact said colorimetric coating or so that a predetermined controlled amount of water or water vapor is permitted to contact said colorimetric coating.

5. An apparatus in accordance with claim 1 wherein each said cassette comprises a frame, at least one of said colorimetric sensor and said collection medium positioned in said frame.

6. A field configurable apparatus for detecting exposure to at least one hazardous substance, said apparatus comprising: a body comprising at least two openings; and
at least two cassettes removably received in said body, each said cassette positioned in one of said openings and comprising at least one of a colorimetric sensor configured to detect the presence of at least one predetermined hazardous substance, and a collection medium configured to collect hazardous substances,
said colorimetric sensor comprising:
a colorimetric layer deposited onto a base layer; and
at least one hydrophobic membrane positioned adjacent said colorimetric layer, said at least one hydrophobic membrane configured to control an amount of gas permitted to penetrate said membrane and contact said colorimetric layer, said at least one hydrophobic membrane attached to at least one of said colorimetric layer and said base layer to seal and prevent water infiltration of said colorimetric layer.

7. An apparatus in accordance with claim 6 wherein each said colorimetric sensor configured to change color upon detection of at least one predetermined hazardous substance.

8. An apparatus in accordance with claim 7 wherein said base layer comprises a hydrophobic film;
said colorimetric layer comprises a colorimetric coating deposited on at least one surface of said base layer.

9. An apparatus in accordance with claim 8 wherein said hydrophobic membrane is configured so that macroscopic water is not permitted to contact said colorimetric coating or so that a predetermined controlled amount of water or water vapor is permitted to contact said colorimetric coating.

10. An apparatus in accordance with claim 7 wherein each said cassette comprises a frame, at least one of said colorimetric sensor and said collection medium positioned in said frame.

11. An apparatus in accordance with claim 6 comprising a plurality of cassettes wherein one cassette is configured to detect the presence of a different hazardous substance from at least one other cassette in said apparatus.

12. An apparatus in accordance with claim 6 further comprising at least one attachment mechanism coupled to said body.

13. A method for detecting a hazardous substance using a field configurable hazardous substance detection apparatus, said method comprising:
positioning a field configurable hazardous substance detection apparatus in an area of interest;
configuring the detection apparatus to detect at least one predetermined hazardous substance; and
monitoring the detection apparatus to determine if a hazardous substance has been detected by the detection apparatus;
the detection apparatus comprising:
a body comprising at least two openings; and
at least two cassettes removably received in said body, each said cassette positioned in one of said openings and comprising a colorimetric sensor configured to detect the presence of a predetermined hazardous substance,
said colorimetric sensor comprising:
a colorimetric layer deposited onto a base layer; and
at least one hydrophobic membrane positioned adjacent said colorimetric layer, said at least one hydrophobic membrane configured to control an amount of gas permitted to penetrate said membrane and contact said colorimetric layer, said at least one hydrophobic membrane attached to at least one of said colorimetric layer and said base layer to seal and prevent water infiltration of said colorimetric layer.

14. A method in accordance with claim 13 wherein said base layer comprises a hydrophobic film;
said colorimetric layer comprises a colorimetric coating deposited on at least one surface of the base layer; and
said configuring the detection apparatus to detect at least one predetermined hazardous substance comprises inserting at least one cassette into the body for each predetermined hazardous substance the user is interested in detecting.

15. A method in accordance with claim 13 wherein said positioning a field configurable hazardous substance detection apparatus in an area of interest comprises attaching the field configurable hazardous substance detection apparatus to a user, to an unmanned apparatus manipulator, or to a surface of a structure.

* * * * *

UNITED STATES PATENT AND TRADEMARK OFFICE
CERTIFICATE OF CORRECTION

| | | |
|---|---|---|
| PATENT NO. | : 8,043,861 B2 | Page 1 of 1 |
| APPLICATION NO. | : 11/226538 | |
| DATED | : October 25, 2011 | |
| INVENTOR(S) | : Edward P. Locke | |

It is certified that error appears in the above-identified patent and that said Letters Patent is hereby corrected as shown below:

Title Pg, Item (73) Assignee: delete "K & M Environmental, Inc., Virginia Beach, VA (US)" and insert therefor -- K & M Environmental, Inc. D/B/A Morphix Technologies, Virginia Beach, VA (US) --

Signed and Sealed this
Twenty-ninth Day of November, 2011

David J. Kappos
*Director of the United States Patent and Trademark Office*